United States Patent [19]
Culross et al.

[11] Patent Number: 6,136,868
[45] Date of Patent: *Oct. 24, 2000

[54] PREPARATION OF HIGH ACTIVITY CATALYSTS; THE CATALYSTS AND THEIR USE

[75] Inventors: Claude C. Culross; Charles H. Mauldin, both of Baton Rouge, La.

[73] Assignee: Exxon Research and Engineering Company, Florham Park, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/153,363

[22] Filed: Sep. 15, 1998

Related U.S. Application Data

[62] Division of application No. 08/847,957, Apr. 22, 1997.

[51] Int. Cl.⁷ .................................................... C07C 27/00
[52] U.S. Cl. ........................ 518/700; 518/709; 518/715; 518/728
[58] Field of Search .................................. 518/700, 709, 518/728

[56] References Cited

U.S. PATENT DOCUMENTS

| | | | |
|---|---|---|---|
| 1,914,557 | 6/1933 | Craver . | |
| 4,234,462 | 11/1980 | Bonder et al. | 252/463 |
| 4,801,573 | 1/1991 | Eri et al. | 502/302 |
| 4,977,126 | 12/1990 | Mauldin et al. | 502/242 |
| 5,064,803 | 11/1991 | Nunan | 502/170 |
| 5,468,709 | 11/1995 | Yamaguchi et al. | 502/210 |

FOREIGN PATENT DOCUMENTS

| | | | |
|---|---|---|---|
| 0601722 | 6/1994 | European Pat. Off. | 45/8 |

*Primary Examiner*—Shailendra Kumar
*Assistant Examiner*—J. Parsa
*Attorney, Agent, or Firm*—Jay Simon

[57] ABSTRACT

A process for the preparation of a catalyst useful for conducting carbon monoxide conversion reactions, especially a Fischer-Tropsch catalyst, use of the catalyst for conducting such reactions, especially Fischer-Tropsch reactions, and the composition produced by said process. In the preparation of the catalyst, a solution of a carbohydrate, or sugar, notably a monosaccharide or disaccharide, particularly sucrose, is employed to impregnate and disperse a compound or salt of a catalytic metal, or metals, e.g., copper or an Iron Group metal such as iron, cobalt, or nickel, or in a preferred embodiment both a compound or salt of rhenium and a compound or salt of a catalytic metal, or metals, e.g., copper or an Iron Group metal such as iron, cobalt, or nickel, onto a refractory inorganic oxide support, e.g., titania. The rhenium, when present only in small amount permits full and complete reduction of the catalytic metal, or metals, dispersed by the carbohydrate. Higher catalyst activities with lower rhenium loadings are thus achieved than in previous preparations where higher concentrations of rhenium were required to both effectively disperse, and reduce the catalytic metal, or metals, during the preparation. Surprisingly, as little as about 1/10 of the rhenium is required to accomplish the reduction promotion where the dispersion is effected with the carbohydrate.

9 Claims, No Drawings

PREPARATION OF HIGH ACTIVITY CATALYSTS; THE CATALYSTS AND THEIR USE

This is a division of application Ser. No. 08/847,957 filed on Apr. 22, 1997.

FIELD OF THE INVENTION

This invention relates to a process, or method, for the production of a high activity catalyst by dispersion of a catalytic metal, or metals, particularly copper or an Iron Group metal, notably cobalt, or both the catalytic metal and rhenium onto a refractory inorganic oxide support, notably titania; the catalyst; its reduction, and use of the catalyst for conducting carbon monoxide hydrogenation reactions, especically Fischer-Tropsch reactions.

BACKGROUND

Carbon monoxide hydrogenation reactions are well known. For example, Fischer-Tropsch synthesis processes, or processes for the catalytic conversion of synthesis gas, i.e., a mixture of hydrogen and carbon monoxide, to high quality distillate fuels or mixtures of $C_5+$ liquid hydrocarbons are well known. For example, the Group VIII non-noble metals, iron, cobalt, and nickel have been widely used to catalyze Fischer-Tropsch reactions, and these metals have been deposited on various supports, and promoted with various other metals. In U.S. Pat. No. 4,568,663, e.g., there is disclosed a process of this type which utilizes a highly active catalyst composition constituted of cobalt-rhenium-titania, $Co-Re-TiO_2$. This catalyst is made, e.g., by impregnating a concentrated aqueous solution of cobalt nitrate and perrhenic acid onto a titania support by the conventional incipient wetness method, drying, and then calcining to decompose the nitrate salt to the oxide. Several important functions are served by the rhenium. A major function is served by rhenium during the calcination of the catalyst, during which cobalt nitrate decomposes to cobalt oxide, in that it causes the cobalt oxide to become more highly dispersed. It also preserves the cobalt oxide in highly dispersed state under high temperature oxidizing conditions, such as is found useful for regenerating cobalt catalysts. It is also a function of the rhenium to lower the temperature of the reduction of cobalt oxide to the zero valence state, which is required to achieve full activity. Rhenium makes it easier to more fully reduce the cobalt. High dispersal, and full reduction of the cobalt results in a more active catalyst. This result however does not come without cost, for rhenium is a relatively expensive commodity. Thus, there exists a need for means to better disperse the cobalt with a lesser amount of rhenium, find means for recovering the rhenium, or find other more available, less expensive materials for promoting the dispersion, and reduction of the metals.

SUMMARY OF THE INVENTION

The present invention, which meets this and other needs, relates to a novel process for the preparation of a catalyst useful for the hydro-genation of carbon monoxide, especially to a Fischer-Tropsch catalyst, the catalyst, and process for the use of this catalyst for conducting such reactions, especially Fischer-Tropsch synthesis reactions, i.e., reactions for the production of $C_5+$ liquid hydrocarbons from hydrogen and carbon monoxide. In the preparation of the Fischer-Tropsch catalyst, a preformed particulate refractory inorganic solids support is impregnated with (a) a compound, or salt, of a catalytic metal, or metals, suitably copper or an Iron Group metal, and (b) a carbohydrate, or sugar, characterized as a monosaccharide or a disaccharide. And, preferably, a preformed particulate refractory inorganic solids support, preferably titania, is impregnated with (a) a compound, or salt, of a catalytic metal, or metals, suitably copper or an Iron Group metal, (b) a carbohydrate, or sugar, characterized as a monosaccharide or disaccharide, and (c) a compound, or salt, of rhenium. In impregnating the support, the support is contacted, preferably, with a single solution containing both (a) and (b), or all of (a), (b), and (c), respectively. The carbohydrate, or sugar, is sufficient to distribute the compound or salt of the catalytic metal, copper or Iron Group metal in highly dispersed form, onto the support; and, the rhenium, when added, is sufficient to produce full reduction of the dispersed metal. Whereas rhenium has been used in the past to produce both of these functions, a far lesser amount of rhenium is required to produce both dispersion and reduction of the metal when the rhenium is used in conjunction with the carbohydrate.

The carbohydrate, or sugar, useful in the practice of this invention is characterized as a monosaccharide, a sugar which will not further hydrolyze on treatment with dilute acids, or a disaccharide, a sugar which will yield two molecules of monosaccharides on hydrolysis. Exemplary monosaccharides include trioses, e.g., glyceraldehyde, dihydroxyacetone and the like; tetroses, e.g., erythrose and the like; pentoses, e.g., arabinose, xylose, ribose and the like; and hexoses; e.g., glucose, mannose, galactose, fructose, sorbose and the like; and useful disaccharides include, e.g., sucrose, maltose, lactose and the like. Of the monosaccharides the pentoses and hexoses, particularly the latter, are preferred, along with the disaccharides. Sucrose is particularly preferred.

It has been found that tile copper or Iron Group metal can be more effectively dispersed onto the support via use of the carbohydrate, or sugar, than with rhenium, as a consequence of which no rhenium is required to effect a full, and complete dispersion of the catalytic metal, or metals. However, some rhenium is generally useful, and sometimes required since its presence enables a more complete and full reduction of the dispersed copper or Iron Group metal to the zero valent state. Accordingly, in the preferred practice of this invention, a small amount of a compound or salt of rhenium, and both a compound or salt of copper or an Iron Group metal and a carbohydrate, or sugar, are employed to disperse the copper or Iron Group metal, and rhenium, onto the solids support component of the catalyst during the impregnation; dispersion of the copper or Iron Group metal into the preformed catalyst resulting from the presence of the carbohydrate, while the rhenium is effective in permitting full reduction of the catalyst after calcination. The copper or Iron Group metal compound, and rhenium compound, are thus effectively dispersed during the impregnation step, and during calcination the carbohydrate, or sugar, is removed by combustion leaving behind crystallites of well dispersed oxides of the copper or Iron Group metal and the rhenium. Essentially complete reduction of the crystallites of the metals is achieved on contact of the calcined catalyst with a reducing agent, e.g., hydrogen. Surprisingly, in the preparation of a catalyst it is found that considerably less rhenium is required overall when prepared with a carbohydrate, or sugar, to produce a full, similar level of activity in a reduced copper or Iron Group metal/rhenium catalyst of given composition, used in a carbon monoxide hydrogenation or Fischer-Tropsch reaction, than with a reduced catalyst of corresponding composition, used in a similar carbon monoxide hydrogenation or Fischer-Tropsch reaction at similar process conditions, made in a preparation otherwise similar except that the catalyst was made without use of a carbohydrate.

DETAILED DESCRIPTION

The catalysts are formed by deposition of the catalytic metal, or metals, on a previously spilled, pelleted, beaded, extruded, spray dried, or sieved support material by the impregnation method. In preparing the catalysts, the metals are deposited from solution on the support in preselected amounts to provide the desired absolute amounts, and weight ratios of the metals being deposited. Catalysts constituted of cobalt and rhenium supported on titania, or a titania-containing support, silica, etc. with or without the addition of an additional metal, or metals, promoter or modifier, e.g., ruthenium, hafnium, zirconium, titanium, chromium, thoria, copper, etc., exhibit superior hydrocarbon synthesis characteristics and provide high selectivities in the conversion of synthesis gas to $C_5+$ hydrocarbon liquids. Suitably, the metals are codeposited by contact and treatment of the support with a solution, suitably an aqueous solution, which contains the carbohydrate, or sugar, e.g., sucrose, in addition to the compound or salt of the copper or Iron Group metal, e.g., cobalt, or the compound or salt of the rhenium, or both the compound or salt of the copper or Iron Group metal and the compound or salt of the rhenium.

The catalytic metal, copper or Iron Group metal, and the rhenium can be deposited from solution in sequence, or codeposited from the same impregnating solution, and the carbohydrate can be deposited from solution in sequence with the copper or Iron Group metal, and rhenium, or codeposited with the copper or Iron Group metal and the rhenium. The carbohydrate can thus be codeposited with a catalytic metal, or metals, or it can be deposited from solution by a separate impregnation. Preferably however, the carbohydrate, or sugar, is codeposited with the copper or Iron Group metal and the rhenium. The volume of impregnating solution used in an impregnation usually ranges from about 1 to about 20 times the volume of the support, and is generally carried out at ambient or elevated temperature. Preferably, the impregnation is carried out at conditions of incipient wetness, and at essentially ambient temperature. In accordance with the incipient wetness technique, as is known, the volume of the impregnating solution and amount of metals is predetermined to correspond to the maximum volume which will just fill the internal pore volume of the support, with no liquid in excess on impregnation of the support. Various refractory inorganic oxide supports are useful in the formation of catalysts pursuant to the practice of this invention. Exemplary of such supports are titania, which is preferred, silica, silica-alumina, alumina, and the like.

Highly concentrated metal salt solutions are most desirable for preparing hydrocarbon synthesis catalysts because they generate the highest metal loading per impregnation, higher metal loadings leading in turn to higher catalytic activity. Common salts or compounds of the catalytic metals can generally be used. However, it has been found that the nitrate salt, especially in the case of cobalt is preferred because it is the most readily available and least expensive salt and, more importantly, it possesses the highest degree of solubility in water. Cobalt acetate is also suitable, although it is less water soluble. Cobalt chloride and sulfate are not suitable for making hydrocarbon synthesis catalysts, presumably because of poisoning by residual anions not removed in the calcination, regardless of the promotion of dispersion by carbohydrates. Solvents other than water may be used, e.g., alcohols, ketones and the like, but are generally not preferred because of lower metal salt solubility and added manufacturing cost. Suitable rhenium compounds are the common water soluble ones, especially perrhenic acid and ammonium perrhenate.

The catalytic metal, copper or Iron Group metal, preferably the latter, and more preferably cobalt, is added to the support in amount sufficient to provide from about 2 percent to about 50 percent, preferably from about 5 percent to about 35 percent of the elemental metal, based on the total weight of the finished catalyst (wt. %; dry basis). The maximum metal loading that can be obtained per impregnation will depend upon the support pore volume, which will in turn depend upon the support composition, and the metal concentration in the impregnating solution. Multiple impregnation/calcination steps may be used to obtain high final metal loadings. Other metals, e.g., thorium, cerium, hafnium, uranium and the like can be added if desired to modify or promote the activity of the finished catalyst. These metals when present are added in weight ratio to copper or Iron Group metal ranging above about 0.01:1, preferably from about 0.025:1 to about 0.1:1. Rhenium is added to the support in concentration sufficient to provide a weight ratio of elemental rhenium:elemental copper or Iron Group metal (e.g., Re/Co weight ratio) in the finished catalyst ranging from about 0.005:1 to about 0.2:1, preferably from about 0.01:1 to about 0.1:1 (dry basis). The carbohydrate is added to the impregnating solution in concentration ranging from about 2 percent to about 20 percent, preferably from about 6 percent to about 15 percent, based on the weight of the total solution; and the solution is contacted with the support to disperse the metal compound, or compounds, onto the support. In such treatment, it disperses the metal, or metals, onto the support even more effectively than the rhenium. The catalyst, after impregnation, is dried by heating, suitably at temperatures ranging from about 30° C. to about 120° C., in an air, nitrogen or other gas stream or under vacuum. The metals are converted to an oxide form by calcination, suitably at temperature ranging from about 200° C. to about 550° C., preferably from about 250° C. to about 400° C., and the carbohydrate is burned, combusted, and removed from the catalyst. The catalyst is then activated by reduction, suitably by contact with hydrogen at temperature ranging from about 250° C. to about 550° C., preferably from about 275° C. to about 425° C., for periods ranging from about 0.5 hour to about 24 hours at pressures ranging from above ambient to about 40 atmospheres.

The catalyst produced in accordance with this invention, particularly those comprised of the Iron Group metals, corresponds in composition to those known, and useful in the conversion of synthesis gas to $C_5+$ hydrocarbons. The Fischer-Tropsch, or hydrocarbon synthesis process is carried out at temperatures of about 160° C. to about 325° C., preferably from about 190° C. to about 260° C., pressures of about 5 atm to about 100 atm, preferably about 10–40 atm and gas hourly space velocities of from about 300 V/Hr/V to about 20,000 V/Hr/V, preferably from about 500 V/Hr/V to about 15,000 V/Hr/V. The stoichiometric ratio of hydrogen to carbon monoxide in the synthesis gas is about 2.1:1 for the production of higher hydrocarbons. However, $H_2$/CO ratios of 1:1 to about 4:1, preferably about 1.5:1 to about 2.5:1, more preferably about 1.8:1 to about 2.2:1 can be employed. These reaction conditions are well known and a particular set of reaction conditions can be readily determined by those skilled in the art. The reaction may be carried out in virtually any type reactor, e.g., fixed bed, moving bed, fluidized bed, slurry, bubbling bed, etc. The waxy, or paraffinic product from the F-T reactor, or reactor utilizing the catalyst made pursuant to the practice of this invention, is an essentially non-sulfur, non-nitrogen, non-aromatics containing hydrocarbon. It is a liquid product which can be produced and shipped from a remote area to a refinery site for further chemically reacting and upgrading to a variety of products, or produced and upgraded to a variety of products at a refinery site. Separator products, i.e., hot separator and cold separator liquids, respectively, $C_4$–$C_{15}$ hydrocarbons, constitute high quality paraffin solvents which, if desired can be hydrotreated to remove olefin impurities, or employed without hydrotreating to produce a wide variety of wax products. The reactor wax, or $C_{16}$ + liquid hydrocarbons from the F-T reactor, on the other hand, can be upgraded by various hydroconversion reactions, e.g., hydrocracking, hydroisomerization, catalytic dewaxing, isodewaxing, etc. or combinations thereof, to produce such products as stable, environmentally benign, non-toxic mid-distillates, diesel and jet fuels, e.g., low freeze point jet fuel, high cetane jet fuel, etc. isoparaffinic solvents, lubricants, e.g., lube oil blending components and lube oil base stocks suitable for transportation vehicles, non-toxic drilling oils suitable for use in drilling muds, technical and medicinal grade white oils, chemical raw materials and various specialty products.

The following non-limiting examples, and comparative demonstrations, exemplify the more salient and preferred embodiments of the invention.

EXAMPLES

A series of catalysts were prepared by impregnating a support, i.e., a rutile and an anatase titania support, and silica, with a concentrated aqueous solution of cobalt nitrate and perrhenic acid via the incipient wetness technique. In most of the preparations, as tabulated hereafter, different carbohydrates were dissolved in cobalt nitrate/perrhenic acid solutions, the carbohydrate generally being added in concentration of greater than 10 wt. % in the impregnating solution. The amount of water present in each impregnating solution was adjusted for the weight of the carbohydrate added to maintain a nearly constant 15 wt. % cobalt, calculated as elemental cobalt, in the solution. In a base case preparation, for comparative purposes, no carbohydrate was added to the cobalt nitrate/perrhenic acid solution. The catalysts were made by single impregnations (about 7 wt. % Co in the finished titania supported catalysts) in the exploration of preparation variables. In each preparation, after impregnation the catalyst was dried and then calcined in air to decompose the nitrate salt to the oxide and burn off the carbohydrate, or organic additive.

The catalyst preparations, or preps, made with a spray-dried titania support were obtained by calcining the raw spray-dried support at two different temperatures, as indicated in the following table. Spray-dried silica supports were also used, and these too are identified in the table.

| Designation | Calcination Temp. ° C. | Surface Area m²/g | H₂O Pore Volume, cc/g |
|---|---|---|---|
| Rutile[1] | 1000 | 19 | 0.33 |
| Anatase[2] | 500 | 29 | 0.50 |
| Silica | 800 | 170/202[3] | 1.02/1.18[3] |

[1] 94% Rutile - 6% Anatase TiO₂
[2] 27% Rutile - 73% Anatase TiO₂
[3] Surface area and H₂O Pore Volume respectively, for silica of Examples 20–22.

Each of the catalysts was characterized by the following tests.

$O_2$ Chemisorption: measured with $O_2$ pulses in helium at 25° C. after reduction in hydrogen at 450° C. Results are expressed as micromoles $O_2$ per gram and as an O/Co atomic ratio. The oxygen chemisorption is a measure of the relative dispersion of cobalt oxide on the support.

Fixed Bed Hydrocarbon Synthesis (HCS) Test: conducted at 200° C., 280 psig, with a syn gas feed of 64H₂-32CO-4Ne and space velocity adjusted as required to give conversion around 70% at 16–20 hours on stream. Catalysts were diluted with 1–7 parts by volume of titania to minimize temperature gradients in a 0.25 inch ID reactor, used to conduct the test. Prior to introducing the syn gas, the catalyst is reduced in situ in hydrogen for one hour at the temperature shown in the Tables. Conversion of CO and selectivity to methane (mole % of CO converted to $CH_4$) are shown in the Tables. Values for "Cobalt Productivity," which has the units of liters of CO converted per hour per gram of cobalt, are also included in each of the Tables.

Table 1: Effect of Carbohydrates As Dispersion Aids—Rutile Titania Support

Table 1 summarizes the results obtained without the use of any carbohydrate, for control purposes, and with different carbohydrates, or organic additives added to the impregnating solution as impregnation aids for dispersing the cobalt throughout a support. The examples were made with the rutile titania support, without any rhenium promoter. The Org/Co mole ratio, column 5 in the Table, presents data which assumes that the disaccharide sucrose is hydrolyzed to glucose and fructose in the highly acidic cobalt nitrate solution (pH≈2). The key results are given in the last column, i.e., reference being made to the O/Co chemisorption data. Example 1 demonstrates for comparative presents a run made without use of any carbohydrate in the preparation. Example 2 also demonstrates for comparative purposes a run made with a saturated starch solution added as an impregnation aid to the impregnating solution. Comparison between Examples 1–2 shows that the added starch is worse than having no carbohydrate at all in the impregnating solution. In Examples 3–8, on the other hand, wherein gluconolactone, glucose, fructose and sucrose were used in the preparations, higher relative dispersions were obtained. These carbohydrates, or sugars, give an O/Co over 0.4 compared to a value of less than 0.3 for the base case. The sugars of this invention, it is believed, improve cobalt dispersion by covering the titania surface with a thin "blanket" of the sugar, which provides a trap for molten anhydrous cobalt nitrate as it is generated in the pores during the drying/calcination process. In the absence of something so polar to bind to, the cobalt salt probably coalesces into larger crystallites as it decomposes to the oxide.

TABLE 1

Carbohydrates As Disperson Aids - Rutile Titania Support

| Example | Organic | grams organic in impreg solution* | Wt % organic in impreg solution | Org/Co mol ratio | Wt % Co | $O_2$ Chemis | O/Co |
|---|---|---|---|---|---|---|---|
| 1 | None | 0 | 0.0 | 0 | 7.06 | 165 | 0.276 |
| 2 | Sat. Starch Solution | 10 | — | — | 6.67 | 127 | 0.225 |
| 3 | Gluconolactone | 4 | 10.4 | 0.23 | 7.37 | 262 | 0.419 |
| 4 | Glucose | 4 | 10.4 | 0.227 | 7.26 | 294 | 0.478 |
| 5 | Fructose | 4 | 10.4 | 0.227 | 7.21 | 254 | 0.416 |
| 6 | Sucrose | 4 | 10.4 | 0.119 | 7.31 | 297 | 0.479 |
| 7 | Sucrose | 5.1 | 13.2 | 0.152 | 7.3 | 291 | 0.470 |
| 8 | Sucrose | 6 | 15.6 | 0.179 | 7.5 | 309 | 0.486 |

*Impreg solution = 28.5 g $Co(NO_3)_2$—$6H_2O$ + x g organic + (10-x) g $H_2O$

Despite the improved cobalt dispersion obtained by dispersion of the sugars onto the titania support, no significant activity will be obtained unless some rhenium is incorporated into the support to promote reduction of the catalyst. Even a small amount of rhenium permits maximization of the hydrocarbon synthesis activity of the catalyst. The sugars function extremely well in generating cobalt dispersion, but the activity of the catalyst does not correspondingly increase unless the reducibility of the dispersed cobalt oxide to the active zero-valent state is improved. Simply applying higher temperature in the reduction step does not solve the problem because the growth of a titania overlayer with titania, or sintering of the cobalt metal in the case of silica, are processes that are favored by higher temperature and counteract any positive gains in reduction. The addition of some rhenium however greatly improved the extent of cobalt oxide reducibility at 375° C.

Table 2. Effect of Rhenium With Sucrose—Anatase Titania Support

Examples 9–10 of Table 2, base case examples not of this invention, show that activity gradually increases with Re:Co ratios up to about 0.09, but there is no further improvement in activity at higher Re:Co ratios. Example 11, data for a run made without any use of rhenium, is compared with Examples 12–14. Examples 12–14, wherein rhenium is added and the sucrose is used in increasing concentration to promote dispersion on the anatase titania support, show a rapid increase in activity as rhenium is introduced into these preps. A Cobalt Productivity well over 5 is achieved with only a 0.04 Re:Co ratio.

Table 3: Effect of Sucrose And Rhenium With Silica Support

Examples 15–19 show that sucrose improves cobalt dispersion on a silica support. In Example 15 no sucrose was added to the impregnating solution, for control purposes; and beginning with Example 16 and continuing through Example 19 sucrose was added in gradually increasing concentration; 2.86 wt.% in Example 16 through 11.45 wt.% in Example 19. As evident from the data, considering first Examples 16 through 18, the O/Co and Co Productivity ratios increased quite rapidly with increasing sucrose concentration. Example 19 shows however that a higher Re/Co ratio, i.e., 0.088, provides no benefit over the lower Re/Co ratio of 0.044 used in Example 18. This lack of sensitivity of the catalyst to rhenium however does not appear to be the case where cobalt is used in higher concentrations. Reference is made to Examples 20–22.

In Example 20 a single impregnation produced a silica catalyst with 17.8 wt. % cobalt, and in Examples 21 and 22 double impregnations produced silica catalysts with 29.5 wt. % and 29.8 wt. % cobalt, respectively. Rhenium was added only to the catalyst of Example 21; the Re/Co ratio being 0.044. In Example 21 it is observed that a relatively high O/Co was obtained, and the cobalt productivity was particularly high; quite high values as compared with those obtained in Examples 20 and 22, respectively.

TABLE 2

Effect of Rhenium with Sucrose - Anatase Titania Support

| Example | Wt % Co | Wt % Re | Re/Co | Wt % Sucrose in impreg soln | $H_2$ Temp | Density | GHSV | CO Conv | Mol % $CH_4$ | Chemis | O/Co | Co Prod |
|---|---|---|---|---|---|---|---|---|---|---|---|---|
| 9 | 16.65 | 0.665 | 0.0399 | 0 | 375 | 1.23 | 3500 | 63 | 7 | 553 | 0.392 | 3.45 |
| 10 | 16.16 | 1.5 | 0.0928 | 0 | 375 | 1.23 | 3400 | 68 | 6.5 | 621 | 0.453 | 3.72 |
| 11 | 16.3 | 0 | 0.0000 | 11.45 | 375 | 1.23 | 2600 | 73 | 4.4 | 392 | 0.284 | 3.03 |
| 12 | 16.66 | 0.052 | 0.0031 | 11.45 | 375 | 1.23 | 3600 | 68 | 4.5 | 488 | 0.346 | 3.82 |
| 13 | 16.59 | 0.309 | 0.0186 | 11.45 | 375 | 1.23 | 6000 | 66 | 4.2 | 690 | 0.491 | 6.21 |
| 14 | 16.73 | 0.7 | 0.0418 | 11.45 | 375 | 1.23 | 5500 | 69 | 4.9 | 699 | 0.493 | 5.90 |

TABLE 3

Effect of Sucrose And Rhenium with Silica Support

| Example | Wt % Co | Wt % Re | Re/Co | Wt % Sucrose in impreg soln | $H_2$ Temp | Density | GHSV | CO Conv | Mol % $CH_4$ | Chemis | O/Co | Co Prod |
|---|---|---|---|---|---|---|---|---|---|---|---|---|
| 15 | 17.4 | 0.77 | 0.044 | 0 | 450 | 0.567 | 2000 | 41 | 7.4 | 776 | 0.526 | 2.66 |
| 16 | 18.1 | 0.8 | 0.044 | 2.86 | 450 | 0.567 | 2000 | 48 | 6.8 | 703 | 0.458 | 2.99 |
| 17 | 18.1 | 0.8 | 0.044 | 5.71 | 450 | 0.567 | 2000 | 62 | 6 | 956 | 0.623 | 3.87 |
| 18 | 18.1 | 0.8 | 0.044 | 11.45 | 450 | 0.567 | 2600 | 70 | 7.1 | 1712 | 1.116 | 5.67 |
| 19 | 17.9 | 1.6 | 0.088 | 11.45 | 450 | 0.567 | 2500 | 68 | 7.1 | 1792 | 1.181 | 5.36 |
| 20 | 17.8 | 0 | 0 | 11.45 | 450 | 0.567 | 2000 | 52 | 7.8 | | | 3.30 |
| 21 | 29.5 | 1.3 | 0.044 | 11.45 | 450 | 0.700 | 6000 | 64 | 6.9 | 2488 | 0.995 | 5.95 |
| 22 | 29.8 | 0 | 0 | 11.45 | 450 | 0.700 | 4500 | 68 | 6.4 | 1666 | 0.660 | 4.69 |

Complete reduction of the catalytic metal, or metals, is required in the use of a titania support to achieve full catalyst activity. Full catalyst activity however can be achieved by the use of only a small amount of rhenium, even at lower reduction temperatures. Surprisingly, as little as 1/10 of the base case amount of rhenium will satisfactorily promote the reduction when the dispersion is accomplished by the presence of the sugar. The copresence of the sugar with the rhenium allows drastic reductions in the amount of rhenium employed while yet achieving full dispersion and reduction of the catalyst.

Having described the invention, what is claimed is:

1. A process for the production of $C_5+$ liquid hydrocarbons from a hydrogen and carbon monoxide synthesis gas by contacting the synthesis gas at reaction conditions with a catalyst prepared by the steps comprising, impregnating a refractory inorganic oxide support with a solution containing (a) a compound or salt, a catalytic metal, or metals; (b) a carbohydrate, or sugar, characterized as a mono saccharide or disaccharide sufficient to disperse the compound, salt, catalytic metal or metals, onto the support, drying and removing the carbohydrate, forming oxides of the metal or metals in the support, and activating the catalyst.

2. The process of claim 1 wherein the catalytic metal or metals impregnated on to the support comprises cobalt.

3. The process of claim 2 wherein at least a portion of the $C_5+$ liquid hydrocarbons are subjected to conversion.

4. The process of claim 3 wherein the conversion is hydroconversion.

5. The process of claim 4 wherein the hydroconversion is hydroisomerization.

6. The process of claim 5 wherein diesel fuels are produced.

7. The process of claim 5 wherein jet fuels are produced.

8. The process of claim 5 wherein the hydroconversion is catalytic dewaxing.

9. The process of claim 8 wherein lube oil base stocks are produced.

* * * * *